United States Patent
Huang et al.

(10) Patent No.: US 9,810,627 B2
(45) Date of Patent: Nov. 7, 2017

(54) FLEXIBLE THREE-DIMENSIONAL LONG-PATH GAS SENSING BY UNMANNED VEHICLES

(71) Applicant: NEC Laboratories America, Inc., Princeton, NJ (US)

(72) Inventors: Ming-Fang Huang, Princeton, NJ (US); Lei Tao, Plainsboro, NJ (US); Yue Tian, Princeton, NJ (US); Ting Wang, West Windsor, NJ (US)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 15/269,586

(22) Filed: Sep. 19, 2016

(65) Prior Publication Data

US 2017/0115218 A1    Apr. 27, 2017

Related U.S. Application Data

(60) Provisional application No. 62/246,821, filed on Oct. 27, 2015.

(51) Int. Cl.
*G01N 21/00* (2006.01)
*G01N 21/59* (2006.01)
(Continued)

(52) U.S. Cl.
CPC .............. *G01N 21/59* (2013.01); *B60R 11/04* (2013.01); *B64B 1/40* (2013.01); *B64C 39/024* (2013.01);
(Continued)

(58) Field of Classification Search
CPC ............. G01N 21/59; G01N 2201/061; G01N 2201/06113; G01N 2201/0612; G01N 2201/062; G01N 2201/0636; G01N 27/4072; G01N 33/0036; G01S 19/13; G01S 17/06; G01S 3/786; B64C 2201/12; B64C 39/024; B60R 11/04; B64B 1/40
(Continued)

(56) References Cited

U.S. PATENT DOCUMENTS

2003/0213912 A1* 11/2003 Tulip ................. G01N 21/3504
250/343
2007/0040121 A1* 2/2007 Kalayeh ............... G01C 11/025
250/342
(Continued)

FOREIGN PATENT DOCUMENTS

CA    WO 2016029305    *   3/2016    ......... G01N 21/3504

OTHER PUBLICATIONS

Chan et al., "NO2 Measurements in Hong Kong using LED Based Long Path Differential Optical Absorption Spectroscopy", Manuscript prepared for Atmos. Meas. Tech. with version 3.2 of the LATEX class copernicus.cls. Date: Feb. 13, 2012, pp. 1-21.
(Continued)

*Primary Examiner* — Sunghee Y Gray
(74) *Attorney, Agent, or Firm* — Jospeh Kolodka (57) ABSTRACT

Systems and methods for generating a three-dimensional gas map includes a remote vehicle including reflective material. A positioning stage including multidimensional movement to track the remote vehicle. A light head to reflect light off of the remote vehicle. A controller to analyze received light to determine gas content and generate a three-dimensional gas map.

1 Claim, 6 Drawing Sheets

(51) Int. Cl.
| | |
|---|---|
| B60R 11/04 | (2006.01) |
| B64B 1/40 | (2006.01) |
| B64C 39/02 | (2006.01) |
| G01S 3/786 | (2006.01) |
| G01S 17/06 | (2006.01) |
| G01S 19/13 | (2010.01) |
| G01S 17/66 | (2006.01) |
| G01S 17/88 | (2006.01) |
| G01S 7/48 | (2006.01) |
| G01N 33/00 | (2006.01) |
| G01N 21/17 | (2006.01) |

(52) U.S. Cl.
CPC ............ *G01S 3/786* (2013.01); *G01S 7/4802* (2013.01); *G01S 17/06* (2013.01); *G01S 17/66* (2013.01); *G01S 17/88* (2013.01); *G01S 19/13* (2013.01); *B64C 2201/12* (2013.01); *G01N 33/0062* (2013.01); *G01N 2021/1795* (2013.01); *G01N 2201/061* (2013.01); *G01N 2201/062* (2013.01); *G01N 2201/0612* (2013.01); *G01N 2201/0636* (2013.01); *G01N 2201/06113* (2013.01)

(58) Field of Classification Search
USPC .......................................................... 356/437
See application file for complete search history.

(56) References Cited

U.S. PATENT DOCUMENTS

2016/0202225 A1* 7/2016 Feng .................. G01N 33/0032
  436/141
2017/0097302 A1* 4/2017 Kreitinger ............ G01N 21/255

OTHER PUBLICATIONS

Khan, et al., "Low Power Greenhouse Gas Sensors for Unmanned Aerial Vehicles", Remote Sensing, May 2012, pp. 1355-1368.
Geyer, et al., Vertical Profiles of NO3, N2O5, O3, and NOx in the Nocturnal Boundary Layer: 2. Model Studies on the Altitude Dependence of Composition and Chemistry, Journal of Geophysical Research, Jun. 2004, pp. 1-18, vol. 109.

* cited by examiner

, 
FLEXIBLE THREE-DIMENSIONAL LONG-PATH GAS SENSING BY UNMANNED VEHICLES

RELATED APPLICATION INFORMATION

This application claims priority to provisional application 62/246,821, filed Oct. 27, 2015 and incorporated herein by reference.

BACKGROUND

Technical Field

The present invention relates to gas sensing and more particularly long-path gas sensing using remote reflective systems.

Description of the Related Art

Trace gas sensing plays a role in many industrial and environmental applications. Gas concentration levels around a facility can inform the owner if the tools and machinery in the facility are functioning properly. Gas concentration level information can also assist in preventing environmental damage by showing that changes need to be made before gas concentration reach harmful or dangerous levels. In certain conditions (such as dealing with dangerous chemicals or volcanoes), the detection location may be too inaccessible or dangerous for human beings to install gas sensing equipment. This makes the gas measurement particularly difficult.

SUMMARY

According to an aspect of the present principles, a system for three-dimensional gas mapping includes a remote vehicle including reflective material on an exterior surface. A positioning stage including multidimensional movement to track the remote vehicle. A light head to reflect light off of the remote vehicle. A controller to analyze received light from the remote vehicle to determine gas content.

According to another aspect of the present principles, a method for three-dimensional gas mapping includes propagating a light beam through air to make a measurement regarding constituents of the air. Tracking a position of a remote vehicle with a tracking source that reflects the light beam off of the remote vehicle. Receiving the light beam reflected off of the remote vehicle. Processing the light beam received and combining with tracking information to produce a three-dimensional gas map.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, systems and methods are provided to employ a remote reflective system for flexible long path gas sensing. Present embodiments provide a spatial mapping of gas concentration over a large area and a three-dimensional (3D) measurement in a relatively short time period. In one embodiment, both horizontal and vertical sensing results can be provided via maneuverability of the remote reflective system. In another embodiment, the remote reflective system may include an unmanned aerial vehicle (UAV). The remote reflective system may also include an unmanned ground vehicle (UGV), a projectile, a manned vehicle, a balloon, a drone, a robot or other movable and controllable reflective surface.

On the remote reflective system side, one embodiment may employ low weight diamond grade reflective tapes to provide signal reflection and enhance the signal strength. In another embodiment, the remote reflective system may use retro reflectors to provide signal reflection and enhance the signal strength. The remote reflective system may employ reflective surfaces to provide signal reflection and enhance the signal strength. In another embodiment, the remote reflective system may carry retro reflector arrays. The remote reflective system's body may be covered by diamond grade retro reflective tape to form a larger reflector.

The remote reflective system's body may include a reflective surface. There need not be an active sensing part on the remote reflective system. Instead, the reflective capabilities may be purely passive, although active maneuvering of the reflective surface is contemplated on the remote device as well. All active components for the gas sensing process including sensor head, light sources and detector for the gas sensing system are separate from the remote reflective system.

In useful embodiments, as the remote reflective system moves in the 3D/2D pattern, a sensor head tracks the location of the remote reflective system using optical feedback and sends the light signal to the remote reflective system. In another embodiment, as the remote reflective system moves in the 3D/2D pattern, the sensor head tracks the location of the remote reflective system using global positioning system (GPS) data and sends the signal light to the remote reflective system. Through the gas mapping system and method, highly flexible optical detection can be achieved with different optical path configurations in real-time. Both horizontal and vertical sensing can be performed. Thus, a 3D mapping of the gas concentration over a large area in a short time period can be achieved. Remote access to dangerous locations can be provided. In addition, the payload of the remote reflective system can be maintained very low, so the remote reflective system may include many commercially available UAV/UGV systems and allow the UAV/UGV longer usage time so the UAV/UGV can travel farther and higher.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 1:
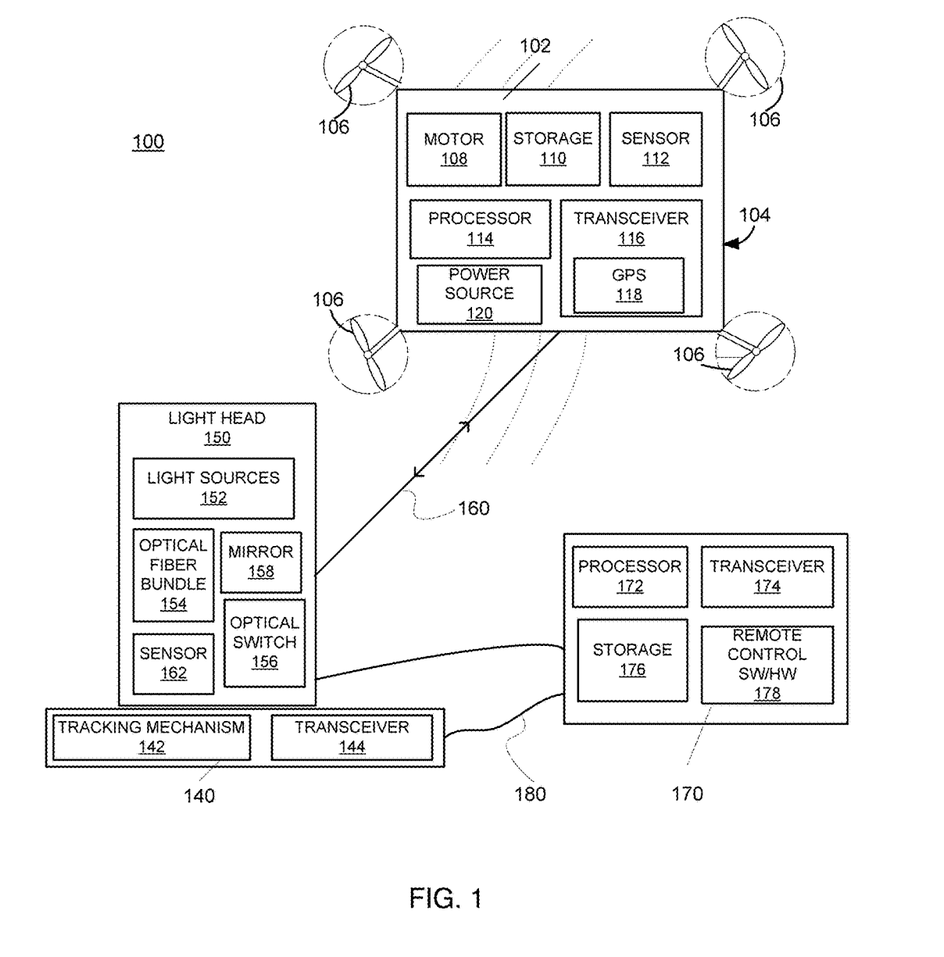
FIG. 1 is a block diagram illustrating a high-level system for a three-dimensional gas mapping system in accordance with the present principles.

Referring now in detail to the figures in which like numerals represent the same or similar elements and initially to FIG. 1, a three-dimensional gas mapping system 100 is illustratively shown. The gas mapping system 100 includes a remote vehicle 102. In one embodiment, the remote vehicle 102 may include an unmanned aerial vehicle (UAV). The UAV allows the three-dimensional gas mapping system 100 to measure gas concentration levels over physically different areas at many different altitudes. In another embodiment, the remote vehicle 102 may include an unmanned ground vehicle (UGV), a projectile, a manned vehicle, a balloon, a drone, a robot or any combination of these and other items.

The remote vehicle 102 includes a reflective surface 104. In one embodiment, the reflective surface 104 may be a retro reflector attached to the remote vehicle 102. In another embodiment, the reflective surface 104 may include reflective tape affixed to the remote vehicle 102. The reflective surface 104 may include the body of the remote vehicle 102 being reflective. The reflective surface 104 may include a mirror attached to the remote vehicle 102 or may include reflective metal attached to the remote vehicle 102. The reflective surface 104 may permit a light beam 160 incident to reflect back to the source of the light beam 160.

The remote vehicle 102 may include a propulsion system 106. For an airborne embodiment, the propulsion system 106 may include propellers or other engines for flying the remote vehicle. In another embodiment, the propulsion system 106 may include wheels or tracks. In another embodiment, the propulsion system 106 may include a jet engine or hoover technology. The propulsion system 106 may include one or more motors 108, which may include an internal combustion engine, electric motor, etc.

The remote vehicle 102 may include a power source 120. The power source 120 may include or employ one or more batteries, liquid fuel (e.g., gasoline, alcohol, diesel, etc.) or other energy source. In another embodiment, the power source 120 may include one or more solar cells or one or more fuel cells. In another embodiment, the power source 120 may include combustive gas (e.g., hydrogen).

The remote vehicle 102 may be equipped with computing functions and controls. The remote vehicle 102 may include a processor 114. The remote vehicle 102 may include a transceiver 116. In one embodiment, the transceiver 116 may be coupled to a global position system (GPS) 118 to generate and alert of a position of the remote vehicle 120 relative to other vehicles and a common coordinate system. The transceiver 116 may be equipped to communicate with a cellular network system. In this way, the remote vehicle's position can be computed based on triangulation between cell towers base upon signal strength or the like. The transceiver 116 may include a WIFI or equivalent radio system.

The remote vehicle 102 may include one or more sensors 112 for making different measurements. The measurements may include pressure, temperature, wind speed, wind direction, speed, acceleration, etc. The sensor 112 may include an optical sensor, an infrared (IR) sensor or a camera. The sensor 112 may include an accelerometer or other motion sensor. It should be understood that the different systems of the remote vehicle 120 may be employed in combination to take or make different measurements needed for the control of the vehicle 102 or locating the vehicle from the ground using telemetry or other techniques.

The remote vehicle 102 may include memory storage 110. The memory storage 110 may include solid state or soft storage and work in conjunction with other systems on the vehicle 120 to record data, run algorithms or programs, control the vehicle, etc. The memory storage 110 may include a Read Only Memory (ROM), random access memory (RAM), or any other type of memory useful for the present applications.

The remote vehicle 102 may be controlled remotely. To be controlled remotely, the remote vehicle 102 needs to be controlled by a remote control device over a wireless channel. This permits the user to dynamically position the remote vehicle 102 where a gas concentration reading is needed. The remote vehicle 102 may follow a preprogrammed path for routine gas concentration checking. In one embodiment, the preprogrammed path may be programmed into the storage 110 to run on the processor 114 to move the remote vehicle 102 in a path designed by the user. The preprogrammed path may be a three-dimensional path from a fixed starting point, like a location of a controller 170 or other location.

The preprogrammed path would be based on global positioning data using, e.g., longitude, latitude, and altitude. In another embodiment, the preprogrammed path can be a closed path. The preprogrammed path may include points in a trajectory, with the remote vehicle 102 moving between the points as efficiently as possible.

The remote vehicle 102 may track and follow a light beam 160. The remote vehicle 102 may use the sensor 112 to detect the light beam 160 and then be programmed to follow the light beam 160 to guarantee that the receiving signals are in best position in a desired location or locations. This allows the user to move the remote vehicle 102 with just changing the position of the light beam 160. The user may be looking at gas concentration readings and observe that a particular area may need a more thorough reading, so the user can keep the remote vehicle 102 in the area by slowly move the light beam 160 and gather more readings for a more thorough gas concentration level.

In another embodiment, the remote vehicle 102 may be programmed to stay a fixed distance from the light source and track its movement, similar to moving along points on a sphere with the light source at the center. The remote vehicle 102 would move to the distance programmed and then follow the light beam 160 while maintain the distance programmed. This allows the user to get gas concentration levels along a dome around the light source. This may be used to sense the gas above the user or may be used to sense the gas in a valley if the user is on a hill next to the valley. This may be used to allow a user to get gas concentration levels for gasses that are denser than air and build up in low areas.

In yet another embodiment, the remote vehicle 102 may follow the light beam 160 while staying fixed in a plane allowing the remote vehicle 102 to move right and left in the plane as well as up and down. The remote vehicle 102 would be programmed with a line that is in the plane, like a longitude, a latitude, or a vector. Then the vehicle would move to the line and the plane above the line would be the limits of the remote vehicle 102 movements while gathering gas concentration levels. The remote vehicle 102 would follow the light beam 160 while maintaining a position in the plane. This may be used to get a gas concentration level over a factory by having the line through the factory and the plane perpendicular to the factory. The user will move the light beam 160 around and the remote vehicle 102 will stay above the factory moving right and left and up and down getting the gas concentration levels above the factory.

The gas mapping system 100 includes a light head 150. The light head 150 may include multiple light sources 152. The multiple light sources 152 may include different sources of light depending on the target gases. In one embodiment, the multiple light sources 152 may include light emitting diodes (LEDs), lasers, ultraviolet (UV) lamps, etc. The LED may be employed for $O_2$ (oxygen), $O_3$ (ozone), $H_2O$, $NO_x$ detection. In another embodiment, the multiple light sources 152 may include a distributed feed-back laser diode (DFB-LD). The distributed feed-back laser diode (DFB-LD) may be employed for CO, $CO_2$, $N_2O$ (nitrous oxide), NO (nitrix oxide), $CH_4$ (methane), HI (hydrogen iodide), HBr (hydrogen bromide), HF (hydrogen fluoride), HCl (hydrogen chloride), $C_2H_2$ (acetylene), HCN (hydrogen cyanide), $H_2S$ (hydrogen sulfide), $NH_3$ (ammonia), $H_2CO$ (formaldehyde) measurements using the appropriate wavelength of light. In another embodiment, the multiple light sources 152 may include a quantum cascaded laser (QCL), which may be used for HBr, HCl, $C_2H_2$, $C_2H_6$ (ethane), $CH_4$, $N_2O$, $NO_2$, NO, $CO_2$, CO, $SO_2$ (sulfur dioxide), HCN, $NH_3$, $H_2CO$, $PH_3$ (phosphine), $O_2$ sensing using the appropriate wavelength of light. In another embodiment, the multiple light sources 152 may include UV lamps, which may be used for NOx, $SO_2$, $O_3$ sensing.

In one embodiment, the light head 150 includes one or more sensors 162, which may include an optical detector, optical sensor, IR sensor, camera, etc. to sense and detect reflected light from the remote vehicle 102. In one embodiment, the light head 150 may include an optical fiber bundle 154 or an optical switch 156. In one embodiment, the light head 150 may include multiple light sources 152 connected to the optical fiber bundle 154 to permit the system to be ready to detect several different gasses without changing parts by using the optical switch 156 to select which of the multiple light sources 152 to use to launch a light beam 160 at the remote vehicle 102. Multiple light beams may be processed concurrently.

In one embodiment, the light head 150 may also include a mirror 158. The mirror 158 may be employed to redirect light to one or more vehicles or other locations on the ground. The mirror 158 may be employed as a telescope to provide both a light beam 160 to the remote vehicle 120 and collect the reflected light beam 160 from the remote vehicle 102. A spherical mirror may be used for mirror 158 to ensure the receiving signals from optical fiber bundle 154 is a focus beam when optical fiber bundle 154 is located at the focus point of mirror 158.

The gas mapping system 100 includes a positioning stage 140. In one embodiment, the positioning stage 140 may include an alt-azimuth mount to allow both vertical and horizontal movement of the light head 150 on the position stage 140. In one embodiment, the positioning stage 140 may have another transceiver 144 to handle communications for remote control of the light head 150 and other functions of the positioning stage 140.

In one embodiment, the transceiver 144 may communicate with a local area network (LAN), cellular system, WIFI system, etc. The positioning stage 140 may be connected wired or wirelessly by connector 180 to the controller 170, and the positioning stage 140 may receive axial adjustment commands from the controller 170 through the connection 180. The axial commands along with the vertical and horizontal movements allow the positioning stage 140 to track or follow the remote vehicle 102 as it travels along the ground or up in the air. In one embodiment, the positioning stage 140 may have a tracking mechanism 142 to provide axial commands, which permit the stage to follow an object on the ground or in the air.

In one embodiment, the tracking mechanism 142 may include a laser tracker. The tracking mechanism 142 allows a user to fly the remote vehicle 102 as high as a measurement is needed and the positioning stage 140 autonomously handles the tracking and gathering of positional information and optical data. In one embodiment, the positioning stage 140 may send telemetry data to the controller 170. The telemetry data may include the position of the remote vehicle 102. The telemetry data can include a three-axis location of the remote vehicle 102 to show where the vehicle 102 was in relation to the positioning stage 140 and how high above the ground the remote vehicle 102 traveled. The telemetry data can be used in creating a map of the locations the remote vehicle 102 was positioned during the gas sensing process.

The gas mapping system 100 includes a controller 170. In one embodiment, the controller 170 may include a processor 172 and memory storage 176 (e.g., disk storage, solid state storage, ROM, etc.). The controller 170 may also include a transceiver 174 to communicate with transceiver 144, etc. The controller 170 may receive GPS data from the remote vehicle 102 to produce axial adjustments for the positioning stage 140. In one embodiment, the controller 170 may include remote control software and hardware 178 to control the remote vehicle 102 to guide the vehicle 120 during the gas mapping process. The remote control software and hardware 178 may include joysticks for a user input and software that accepts input from the joysticks and outputs commands for a remote controlled vehicle. The remote control software and hardware 178 may include a wire or an antenna for a wireless connection to the remote vehicle 102, and the software to modulate the output commands as a signal along the connection. In one embodiment, the remote control software and hardware 178 may be employed to guide the vehicle 120 by a user input using the controller 170. In another embodiment, the remote control software and hardware 178 may send preprogrammed commands to the remote vehicle 102 to guide the vehicle 120 along a predefined path.

The controller 170 may employ telemetry data from the positioning stage 140 to produce a map of the remote vehicle's 102 location during the gas sensing process. The controller 170 may employ the GPS data from the remote vehicle 102 to produce a map of remote vehicle's 102 location during the gas sensing process or use the preprogrammed path of the remote vehicle 102 to produce a map of remote vehicle's 102 location during the gas sensing process. Each map can include a three-axis map to show the remote vehicles position as it moves through and above the area that gas sensing is being processed. These maps may be overlaid on top of existing satellite or topographical maps of the gas sensing area to better show where the remote vehicle 102 traveled during the gas sensing process.

In one embodiment, the controller 170 may receive optical data from the light head 150 based on the reflected light beam 160 from the remote vehicle 102. The controller 170 may process this optical data to calculate the concentration of detected gasses by the remote vehicle 102 using known optical spectroscopic techniques based on the light source 152. One technique may take the value of the gas sensed at neighboring points to calculate the gas at the actual point, since the value of gas sensed is for all the gas found along the entire path of the light beam 160. In one embodiment, the controller 170 may combine the detected gasses with the map to form a three-dimensional gas map of gas concentration levels in the area that the remote vehicle 102 occupied during the gas sensing process. The three-dimensional gas map may be colored or textured on top of a surface area map showing concentrations of a sensed gas or an interactive three-dimensional map that allows a user to rotate the map to see the different gas levels based on the users controlling perspective.

Figure 2:
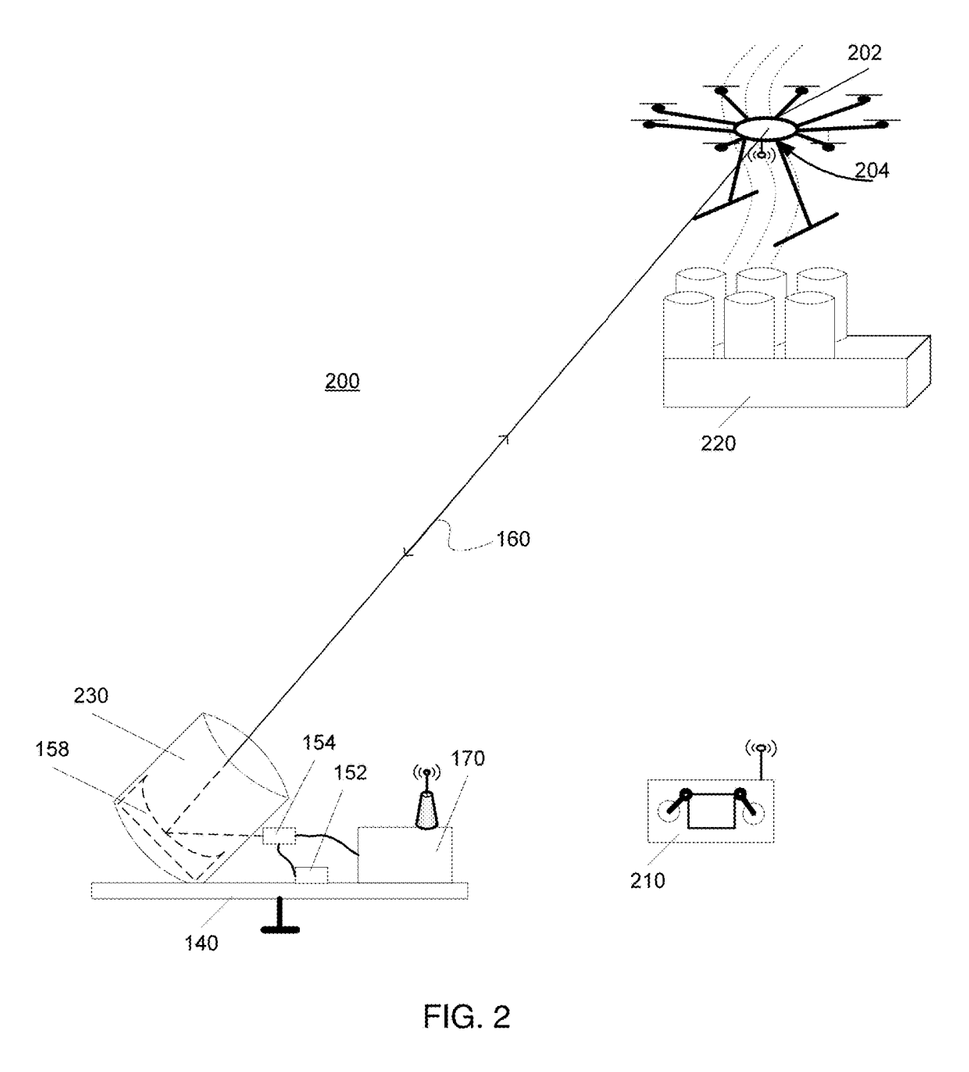
FIG. 2 is a block diagram illustrating a system for a three-dimensional gas mapping system in accordance with the present principles.

Referring to FIG. 2, a three-dimensional gas mapping system 200 is illustratively depicted in accordance with an embodiment of the present principles. The three-dimensional gas mapping system 200 may include a UAV 202 with diamond grade reflective tape 204 affixed to the UAV body, and some or all of the following: a telescope 230 with a mirror 158, an optical fiber bundle 154 with a light source 152, a controller 170, a positioning stage 140, and a remote control device 210. The UAV 202 can fly over the source 220 of the gas to be measured. The source of gas may include a factory, a farm, a power plant, a methane recovery site, a city, or any site where gas concentration levels are useful. The UAV 202 is controlled by the remote control device 210. The remote control device 210 gives the user the ability to move the UAV 202 to the locations that need to have the gas measured. The UAV 202 makes getting measurements at ground level or hundreds of feet in the air possible, plus it allows for easy moving around the site. The light source 152 sends light through the optical fiber bundle 154 into the telescope 230. The light reflects off the mirror 158 to have a light beam 160 shine on the UAV 202. The diamond grade reflective tape 204 will reflect the light beam 160 back to the optical fiber bundle 154 through the telescope 230. The optical data from the light beam 160 is sent to the controller 170 for analysis.

The controller 170 determines the gas detected based on the light source 152 using optical spectroscopic techniques (e.g., differential optical absorption spectroscopy (DOAS)) or attenuation data (e.g., wavelength modulation spectroscopy (WMS)). The controller 170 receives GPS data from the UAV 202 while receiving the optical data to form a map. The map would be a three-axis map to show the remote vehicles position as it moves through the area that gas sensing is being processed. This map may be overlaid on top of existing satellite maps to show where the vehicle sensed gas during the process along all three-axis, longitude, latitude, and altitude. The controller 170 combines the gas concentration data with the map to form a three-dimensional gas map of the area showing detected gas levels.

Figure 3:
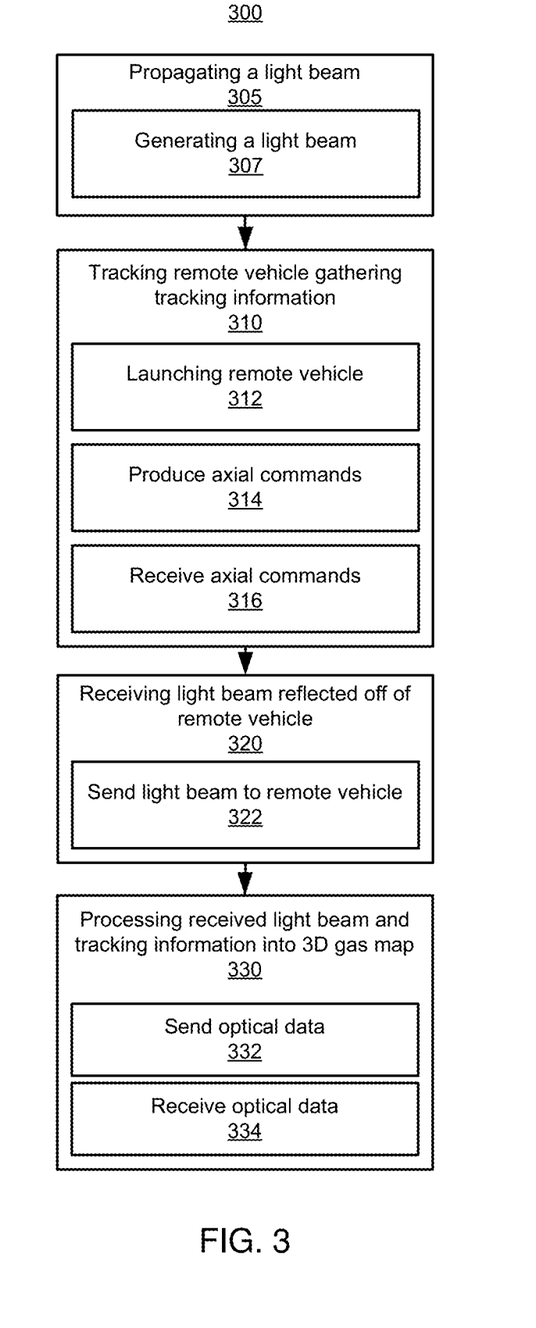
FIG. 3 is a flow diagram illustrating a method for generating a three-dimensional gas map in accordance with the present principles.

Referring to FIG. 3, a flow chart for a method to generate a three-dimensional gas map 300 is illustratively shown in accordance with the present principles. The methods to generate a three-dimensional gas map 300 may include propagating a light beam through air to make a measurement regarding constituents of the air in block 305. The light source, including wavelength of light, may vary depending on the gas to be measured. In one embodiment, propagating a light beam through air, in block 305, may include generating the light beam in block 307. The methods to generate a three-dimensional gas map 300 may include tracking a remote vehicle with a tracking source that gathers tracking information in block 310. The tracking information may be used to guide the light beam as the remote vehicle moves. In one embodiment, the remote vehicle is tracked in block 310, which may include launching the remote vehicle in block 312. In another embodiment, the tracking the remote vehicle in block 310 may include producing axial commands in block 314 with a control system. The axial commands may be produced to guide the light beam to the remote vehicle.

In yet another embodiment, the tracking the remote vehicle in block 310 may include receiving axial commands in block 316 from a control system. The axial commands may be used to guide the light beam to the remote vehicle. The method to generate a three-dimensional gas map 300 may include receiving a light beam reflected off of the remote vehicle in block 320. In one embodiment, the receiving the light beam in block 320 may include sending a light beam to the remote vehicle in block 322. The sending a light beam will use the tracking information to aim the light beam at the remote vehicle.

Generating a three-dimensional gas map 300 may include processing the received light beam and the tracking information to produce a three-dimensional gas map in block 330. The received light beam will be processed for detected gas along the light beam between the light source and the remote vehicle. The detected gas will be plotted according the tracking information to produce a map of the detected gasses around the remote vehicle will the gas sensing process was being completed. This detected gas map can be overlaid on a satellite or topographic map to show the gas concentration levels in relation to the physical world represented by the satellite or topographic maps, including the altitude that the gas concentration exists. In one embodiment, the processing in block 330 may include sending optical data to a control system in block 332. In one embodiment, the processing in block 330 may include receiving optical data with a control system in block 334. The gas detection processing and map processing may be completed in a control system.

Figure 4:
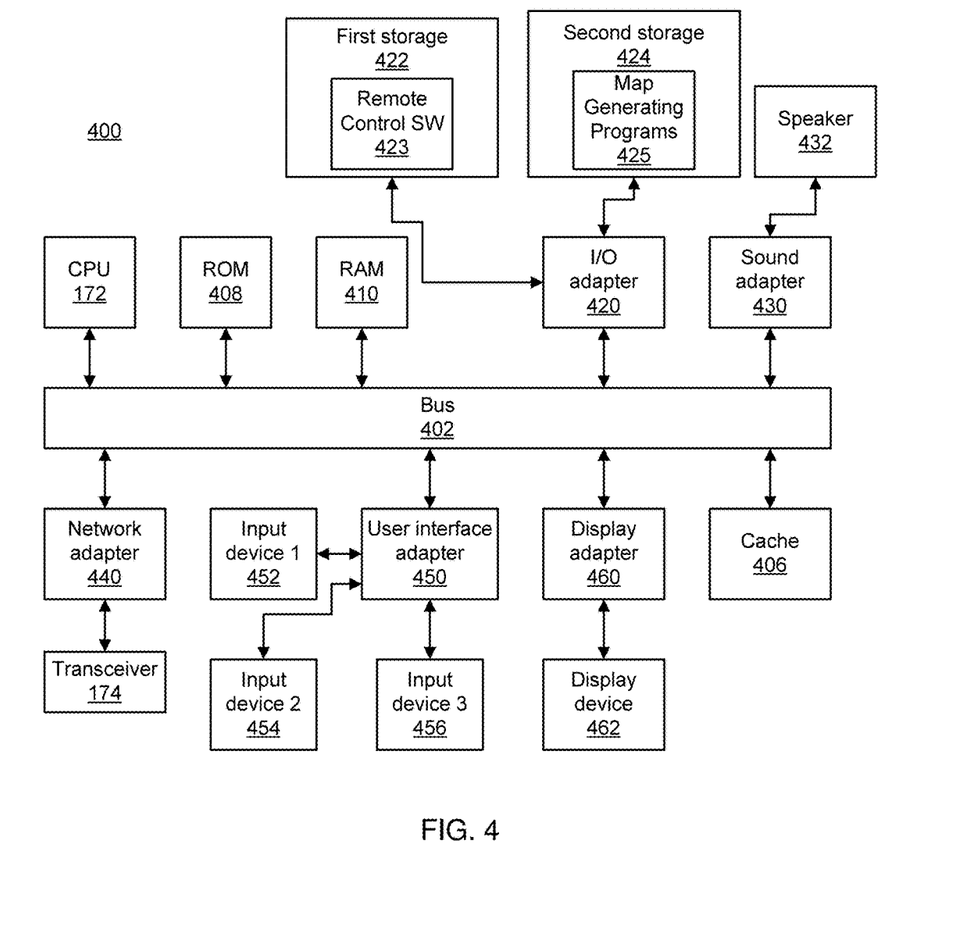
FIG. 4 is a block diagram illustrating a controller for a three-dimensional gas mapping system in accordance with the present principles.

Referring to FIG. 4, an exemplary control system 400 is shown which may represent the controller 170 (FIG. 1). The control system 400 includes at least one processor (CPU) 172 operatively coupled to other components via a system bus 402. A cache 406, a Read Only Memory (ROM) 408, a Random Access Memory (RAM) 410, an input/output (I/O) adapter 420, a sound adapter 430, a network adapter 440, a user interface adapter 450, and a display adapter 460, are operatively coupled to the system bus 402.

A first storage device 422 and a second storage device 424 are operatively coupled to system bus 402 by the I/O adapter 420. The storage devices 422 and 424 can be any of a disk storage device (e.g., a magnetic or optical disk storage device), a solid state magnetic device, and so forth. The storage devices 422 and 424 can be the same type of storage device or different types of storage devices. In one embodiment, the first storage device 422 or the second storage device 424 may include remote control software 423 to control the remote vehicle. The remote control software 423 may be able to access the hardware necessary to get user inputs and output a control command to the remote control vehicle, like a joystick or an antenna. The remote control software 423 may be able to take a user input from an input device, like a joystick, and output a command to control the movement of the remote control vehicle in the direction intended by the movement of the joystick by the user.

In another embodiment, the first storage device 422 or the second storage device 424 may include map generating programs 425. The map generating programs 425 may be able to take GPS, telemetry, or path information to plot in a three-dimensional axis to form a map. The map generating programs 425 may take a produced map an overlay it on existing satellite or topographic maps to show the locations traveled gathering the data in relation to the physical world.

In yet another embodiment, the first storage device 422 or the second storage device 424 may include optical data analyzing programs. The optical data analyzing programs may take light beam data in to calculate the level of gas the light beam traveled through. In yet another embodiment, the first storage device 422 or the second storage device 424 may include path generating programs. The path generating programs may create a three-dimensional path for a remote vehicle to travel based on user input coordinates.

A speaker 432 may be operatively coupled to system bus 402 by the sound adapter 430. The speaker 432 may be used to give the user an auditory warning of low fuel or power. A transceiver 174 is operatively coupled to system bus 402 by network adapter 440. A display device 462 is operatively coupled to system bus 402 by display adapter 460.

A first user input device 452, a second user input device 454, and a third user input device 456 are operatively coupled to system bus 402 by user interface adapter 450. The user input devices 452, 454, and 456 can be any of a keyboard, a mouse, a keypad, a joystick, an image capture device, a motion sensing device, a microphone, a device incorporating the functionality of at least two of the preceding devices, and so forth. Of course, other types of input devices can also be used, while maintaining the spirit of the present principles. The user input devices 452, 454, and 456 can be the same type of user input device or different types of user input devices. The user input devices 452, 454, and 456 are used to input and output information to and from system 400.

Of course, the control system 400 may also include other elements (not shown), as readily contemplated by one of skill in the art, as well as omit certain elements. For example, various other input devices and/or output devices can be included in control system 400, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the control system 400 are readily contemplated by one of ordinary skill in the art given the teachings of the present principles provided herein.

Figure 5A:
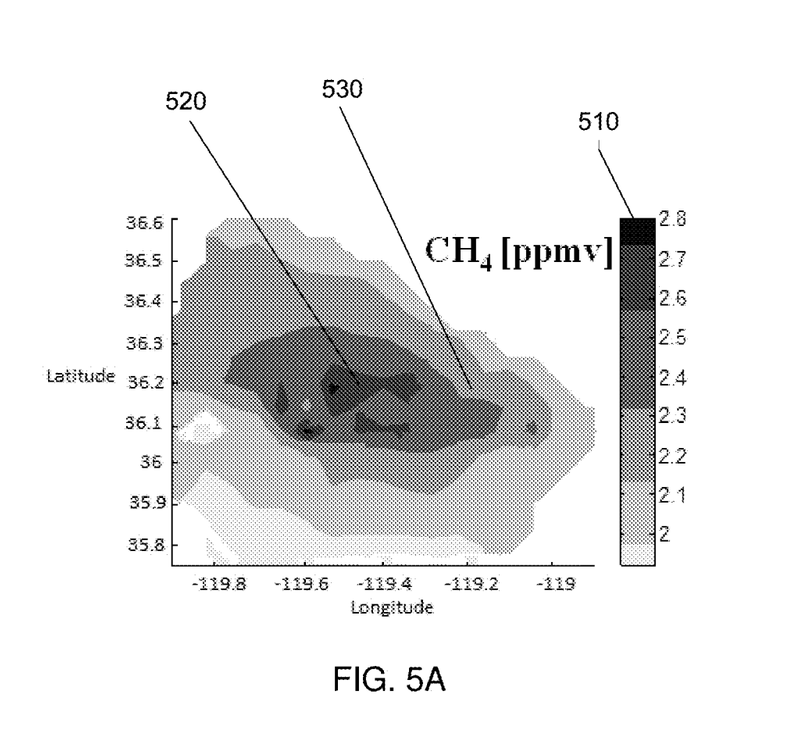
FIG. 5A is a graph of a methane gas concentration map with the x-axis being latitude in degrees and the y-axis being longitude in degrees.

Referring to FIG. 5A, a graph of a methane gas concentration map is illustratively shown. The map shows the concentration of methane ($CH_4$) over an area. The axes of the map are longitude (x-axis) and latitude (y-axis) showing a specific location. The key 510 of the map shows the levels of gas represented by varying shades or color, though a color scale or texture/pattern scale may be employed. The map shows a high concentration of methane around latitude 36.2° and longitude −119.5°. The map shows a higher concentration at 520 and a lower concentration at 530. This shows the cumulative methane concentration at that location from the ground up. The methane can be at ground level or hundreds or feet above ground level.

Figure 5B:
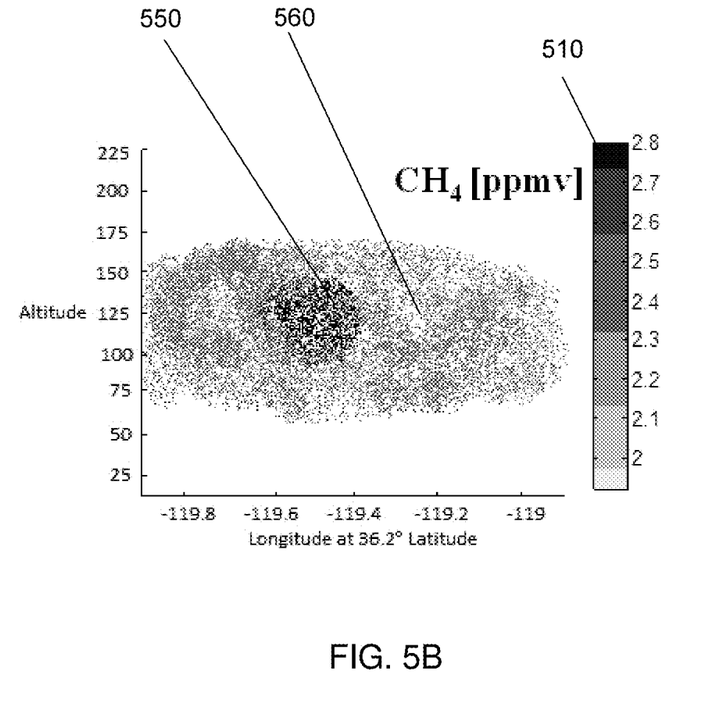
FIG. 5B is a graph of a methane gas concentration map with the x-axis being altitude in feet and the y-axis being longitude in degrees.

Referring to FIG. 5B, a graph of a methane gas concentration map is illustratively shown. The map shows the location of the methane concentration along latitude 36.2° for the same longitude represented in FIG. 5A. The axes of the map are altitude (x-axis) and longitude (y-axis), the altitude is measured as above ground level though it could be measured as above sea level. The key 510 of the map shows the levels of gas represented by varying shades of grey, though a color scale or texture/pattern scale could be used. The key 510 is the same as FIG. 5A. The map shows that the methane is concentrated in the between 75 and 150 feet along latitude 36.2°. The map shows a higher concentration at 550, between −119.4° and −119.6° longitude and 100 to 150 feet, and a lower concentration at 560, between −119° and −119.2° longitude and 100 to 150 feet. FIGS. 5A and 5B are two-dimensional illustrations of the three-dimensional map generated by the three-dimensional mapping process.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A system for three-dimensional gas mapping, comprising:

a remote vehicle including reflective material on an exterior surface;

a positioning stage including multidimensional movement to track the remote vehicle;

a light head to reflect light off of the remote vehicle; and a controller to analyze received light from the remote vehicle to determine gas content;

wherein the reflective material includes a diamond grade reflective tape.

* * * * *